United States Patent

Senaratne et al.

[11] Patent Number: 5,856,597
[45] Date of Patent: Jan. 5, 1999

[54] PREPARATION OF LUCAS REAGENT OF ENHANCED UTILITY AND ITS USE IN SYNTHESIS OF CYCLOALIPHATIC CHLORIDES

[75] Inventors: K. Pushpananda A. Senaratne; Felix M. Orihuela; Arcelio J. Malcolm, all of Baton Rouge, La.

[73] Assignee: Albemarle Corporation, Richmond, Va.

[21] Appl. No.: 846,095

[22] Filed: Apr. 25, 1997

[51] Int. Cl.$^6$ .................................................. C07C 17/16
[52] U.S. Cl. ........................................... 570/261; 570/258
[58] Field of Search ..................................... 570/258, 261

[56] References Cited

U.S. PATENT DOCUMENTS 4,073,816  2/1978  Herrmann ................................. 570/258

OTHER PUBLICATIONS

Chemistry of Organic Compounds, Carl R. Noller, 1965, Chapter 8, p. 148.

*Primary Examiner*—Alan Siegel
*Attorney, Agent, or Firm*—Philip M. Pippenger

[57] ABSTRACT

Gaseous anhydrous hydrogen chloride is introduced into an aqueous solution of zinc chloride under conditions effective to produce a more efficient Lucas reagent than a Lucas reagent made by mixing solid, anhydrous zinc chloride with 38% hydrochloric acid. For example, the reaction rate of such Lucas reagent with levo-menthol is much faster and requires a much shorter reaction period than Lucas reagent formed in the conventional manner from anhydrous, solid zinc chloride and concentrated (38%) hydrochloric acid. Also, the conversion to levo-menthyl chloride was higher when using Lucas reagent formed using gaseous anhydrous hydrogen chloride and aqueous zinc chloride solution. Also, Lucas reagent made in this manner is highly amenable to recycling, and requires only addition thereto of hydrogen chloride to replenish the catalyst for an ensuing run.

12 Claims, No Drawings

PREPARATION OF LUCAS REAGENT OF ENHANCED UTILITY AND ITS USE IN SYNTHESIS OF CYCLOALIPHATIC CHLORIDES

TECHNICAL FIELD

This invention relates to a novel, highly efficient process for the preparation of Lucas reagent having superior properties and utility in the synthesis of certain cycloaliphatic chlorides as compared to Lucas reagent made in the conventional manner. Improvements in the synthesis of o-alkyl-substituted monochlorocycloalkanes using Lucas reagent prepared pursuant to this invention also forms part of this invention.

BACKGROUND

Conventional Lucas reagent is a solution of zinc chloride in concentrated hydrochloric acid, and is made by reacting solid, anhydrous zinc chloride with 38% hydrochloric acid. One important utility for conventional Lucas reagent has been its use in reaction with menthol to form menthyl chloride, which in turn is used in the manufacture of neomenthyl diphenyl phosphine, a ligand useful in formulating catalysts used in the manufacture of certain non-steroidal antiinflammatory drugs.

THE INVENTION

Surprisingly, a way has now been found of preparing Lucas reagent which possesses superior properties and utility in the synthesis of certain cycloaliphatic chlorides as compared to Lucas reagent prepared in the conventional manner.

Thus in one of its embodiments, this invention provides a process which comprises introducing gaseous anhydrous hydrogen chloride into an aqueous solution of zinc chloride under conditions effective to produce a more efficient and/or useful Lucas reagent than Lucas reagent made in the conventional manner by reacting solid, anhydrous zinc chloride with 38% hydrochloric acid. The conditions under which Lucas reagent is formed pursuant to this invention are readily achieved. Thus the gaseous anhydrous hydrogen chloride is introduced into a water solution formed by dissolving at least 60 parts by weight of zinc chloride ($ZnCl_2$) in 40 parts by weight of water, and preferably at least about 70 parts by weight of zinc chloride in 30 parts by weight of water. The solution can be saturated or even super-saturated with the zinc chloride, but preferably the solution is free of solids. During the introduction of the anhydrous hydrogen chloride gas into the zinc chloride solution the temperature of the reaction mixture is maintained at one or more temperatures in the range of about 10° to about 60° C., and preferably at one or more temperatures in the range of about 20° to about 40° C. at ambient atmospheric pressure. The amount of anhydrous hydrogen chloride gas introduced into the zinc chloride solution should be in the range of slightly above 1 mole (e.g., 1.05 moles) up to about 2 moles per mole of zinc chloride. Preferably the amount of HCl gas used is in the range of slightly above 1 mole to about 1.5 moles per mole of zinc chloride.

Another embodiment of the invention is a process which comprises mixing together (i) Lucas reagent formed as described above, and (ii) a cycloaliphatic alcohol of the formula ROH wherein R is a mono- or polyalkyl-substituted cycloalkyl group having from 5 to 8 carbon atoms in the ring and having a linear or branched alkyl group of up to about 12 carbon atoms substituted on one of the ortho positions of the ring relative to the ring carbon atom substituted by the hydroxyl group, such that the corresponding cycloaliphatic chloride of the formula RCl is formed. By use of Lucas reagent formed in accordance with this invention in lieu of Lucas reagent formed in the conventional manner from anhydrous, solid zinc chloride and concentrated (38%) hydrochloric acid, the reaction rate of the reaction with the cycloaliphatic alcohol is much faster and thus a much shorter reaction period is required to produce the cycloaliphatic chloride. For example, a reaction between levo-menthol and Lucas reagent formed according to this invention can be completed on a laboratory scale in one hour with a conversion to levo-menthyl chloride of greater than 98%. In contrast, a reaction conducted in substantially the same general manner but using the Lucas reagent made in the conventional manner required about 5 hours and even so, the yield of levo-menthyl chloride was 91.5%.

Another feature of the invention is that Lucas reagent made pursuant to this invention is highly amenable to recycling, and thus is readily recycled in the foregoing process for the production of cycloaliphatic chlorides.

These and other embodiments and features of the invention will be still further apparent from the ensuing description and appended claims.

FURTHER DETAILED DESCRIPTION

The o-alkyl-substituted cycloaliphatic alcohols as described above can have, in addition to the ortho-alkyl substitution, other ring substituents which are innocuous in the sense that they will not impair or inhibit the desired reaction. While such additional substituents can be in any positions which do not unduly sterically hinder the hydroxyl group, such substituents are preferably in the meta or para positions relative to the hydroxyl substitution. Examples of such innocuous substituents include alkyl groups, alkenyl groups, hydrocarbyloxy groups, hydrocarbylthio groups, hydrocarbylcarbonyl groups, hydrocarbyloxyhydrocarbyl groups, and heteroaromatic groups, dihydrocarbylamino groups, and combinations of two or more of these. Typically in the practice of this invention, this reactant will contain a total of up to about 24 carbon atoms, and preferably up to about 18 carbon atoms, in the molecule. As regards ring size, most preferably the ring is a 6-membered ring. The ortho-alkyl substituent is preferably a secondary alkyl group which most preferably contains up to about 6 carbon atoms. A particularly preferred reactant is menthol, most preferably levo-menthol.

Reaction between the Lucas reagent formed pursuant to this invention and the o-alkyl-substituted cycloaliphatic alcohol is typically conducted at one or more temperatures in the range of about 10° to about 60° C., and preferably at one or more temperatures in the range of about 20 to about 40° C. Normally the reaction is performed at normal ambient atmospheric pressure, but it can be conducted at elevated pressures if desired. Proportions typically fall in the range of about 0.2 to about 0.4 moles of the cycloaliphatic alcohol per mole of zinc chloride used in forming the quantity of Lucas reagent being used in the reaction. Preferably these proportions are in the range of about 0.30 to about 0.35 moles of the cycloaliphatic alcohol per mole of zinc chloride used in forming the quantity of Lucas reagent being used in the reaction. When conducted at room temperature and atmospheric pressure, the reaction is typically complete in less than about one hour.

Most preferably the cycloaliphatic alcohol is added to freshly prepared Lucas reagent formed according to this invention, and the resultant mixture is suitably agitated or stirred to ensure thorough mixing. However, other modes of addition can be used, such as concurrent co-feeding of the Lucas reagent and the cycloaliphatic alcohol into a suitable reaction vessel, or adding the Lucas reagent to the cycloaliphatic alcohol, or combinations of any such procedures.

Workup of the reaction mixture to recover the cycloaliphatic chloride can be conducted in various ways. A preferred workup procedure involves mixing with the reaction mixture a suitable organic solvent such as one or more inert liquid hydrocarbon solvents, such as one or more liquid paraffinic, cycloparaffinic and/or aromatic hydrocarbons, or similar inert solvents. The organic and residual aqueous phases are separated from each other. After drying the organic phase, the organic solvent and the cycloaliphatic chloride are separated from each other, preferably by distillation. Typically the organic solvent selected for use boils at one or more temperatures well below that of the cycloaliphatic chloride so that the solvent can be readily stripped off from the cycloaliphatic chloride at reduced pressure.

Recycle of the Lucas reagent formed pursuant to this invention is readily effected by treating the above separated residual aqueous phase with additional anhydrous hydrogen chloride to form fresh Lucas reagent pursuant to this invention. Thereupon the freshly formed Lucas reagent is used in another reaction with fresh cycloaliphatic alcohol. This procedure can be repeated over and over. Gradual loss, if any, of zinc values from the Lucas reagent during repeated usage can be made up by addition of zinc chloride to the separated residual aqueous phase whenever deemed necessary or desirable.

The following examples, in which percentages are by weight, are presented for the purposes of illustration and not limitation. In Example I, Part B represents the invention. Example II illustrates the advantageous facile recyclability of the Lucas reagent formed pursuant to this invention.

EXAMPLE I

PART A—Preparation of Menthyl Chloride from Menthol and Lucas Reagent Made in the Conventional Manner Solid anhydrous $ZnCl_2$ (306.3 g, 2.25 mols) was dissolved in ice cold concentrated hydrochloric acid (209 mL, 2.52 mols). This solution was warmed to room temperature and levo-menthol (117 g, 0.750 mols) was added in one portion. The resulting heterogenous mixture was stirred for five hours at ambient temperature. The organic phase was removed and the aqueous phase was extracted with petroleum ether having a boiling range of 35°–60° C. After mixing the petroleum ether phase with the original organic phase, the mixed organic phase was extracted with water (2×35 mL) followed by repeated extractions with concentrated $H_2SO_4$ (8×35 mL). The organic phase was washed again with water (5×35 mL), and then dried over anhydrous $MgSO_4$. The desiccant was filtered off, and the filtrate was concentrated under reduced pressure to obtain menthyl chloride in 91.5% yield and >97% purity (GC area %).

PART B—Preparation of Lucas Reagent Pursuant to the Invention, and its Use in the Preparation of Menthyl Chloride from Menthol Pursuant to the Invention Anhydrous HCl gas was bubbled into a 70% aqueous solution of $ZnCl_2$ formed from 0.256 mol of $ZnCl_2$. Levo-menthol (12 g, (77 mmols) was added to the resultant Lucas reagent, and the mixture was stirred for 1.0 hour. The reaction mixture was then treated with petroleum ether and extracted with water. The combined organic phase was dried and stripped under vacuum to remove the solvent. The GC analysis of the reaction mixture showed >98% conversion of menthol to menthyl chloride.

Part C—Preparation of Menthyl Chloride with $ZnCl_2$ (70%) and Aqueous HCl

To concentrated hydrochloric (11 mL, 0.144 mol) was added 70% $ZnCl_2$ solution (17.5 g, 0.129 mol), followed by levo-menthol (7 g, 40 mmols). It was noted that the reaction was slow.

EXAMPLE II

Making Menthyl Chloride in Successive Runs with Recycle of Lucas Reagent Made per the Invention Into a 70% aqueous solution of $ZnCl_2$ formed from 25 g, (0.13 mol) of $ZnCl_2$ was bubbled gaseous anhydrous HCl (5.5 g, 0.15 mol) to form a Lucas reagent of the invention. After addition thereto of crystalline levo-menthol (6 g, 38.5 mmols) the mixture was stirred at ambient temperature for 20 minutes. The organic phase was analyzed for menthyl chloride, which indicated that the conversion of menthol to menthyl chloride was >97%. The organic phase was removed. After anhydrous HCl (2.8 g, 77 mmols) was bubbled into the aqueous phase, another 6 g of levo-menthol was added thereto and the resultant mixture was stirred for 20 minutes at ambient temperature. GC analysis again showed the conversion was >97%. This process was repeated for two more cycles giving the same results. Thus the Lucas reagent formed per this invention was readily recycled from run to run simply by supplying only makeup HCl. Moreover, the activity of the reagent was not diminished for at least these four reaction cycles.

Although well known to those skilled in the art, it is deemed necessary, or at least prudent, to point out that because the water solutions of zinc chloride are referred to herein, the "zinc chloride", or at least a substantial proportion thereof, exists in ionic form while dissolved in the water. Thus according to known chemical principles, the water contains zinc cations and chloride anions. However chemists would commonly refer to this as forming a zinc chloride solution because upon removal of water, zinc chloride would indeed exist as such. Thus when referring in the specification and claims hereof to zinc chloride in aqueous or water solution it is to be understood that the reference is to the substance in whatever chemical form it exists while in such solution under the conditions being used. In short, this disclosure and the claims thereof are to be read with the application of common sense and with at least a rudimentary knowledge of the field of chemistry.

It is to be understood that the reactants and components referred to by chemical name or formula anywhere in the specification or claims hereof, whether referred to in the singular or plural, are identified as they exist prior to coming into contact with another substance referred to by chemical name or chemical type (e.g., another reactant, a solvent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical reaction or in forming a mixture to be used in conducting a desired reaction. Accordingly, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. The fact that a substance, component or ingredient may have lost its original identity through a chemical reaction or transformation during the course of contacting, blending or mixing operations, if conducted in accordance with this disclosure and with the application of common sense and the ordinary skill of a chemist, is thus wholly immaterial for an accurate understanding and appreciation of the true meaning and substance of this disclosure and the claims thereof.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A process which comprises mixing together:
   A) a Lucas reagent formed by a process which comprises introducing gaseous anhydrous hydrogen chloride into an aqueous solution of zinc chloride under conditions effective to produce a more efficient Lucas reagent than a Lucas reagent made by reacting solid, anhydrous zinc chloride with 38% hydrochloric acid, and
   B) a cycloaliphatic alcohol of the formula ROH wherein R is a mono- or polyalkyl-substituted cycloalkyl group having from 5 to 8 carbon atoms in the ring and having a linear or branched alkyl group of up to about 12 carbon atoms substituted on one of the ortho positions of the ring relative to the ring carbon atom substituted by the hydroxyl group;
   such that a reaction mixture containing the corresponding cycloaliphatic chloride of the formula RCl is formed.

2. A process according to claim 1 wherein said reaction mixture is resolved into (i) an organic phase containing said cycloaliphatic chloride, and (ii) an aqueous residual catalyst phase, and wherein said phases are separated from each other.

3. A process according to claim 2 wherein the aqueous residual catalyst phase is treated with additional anhydrous hydrogen chloride to form fresh Lucas reagent for use in conducting another reaction with cycloaliphatic alcohol of B) to form another quantity of cycloaliphatic chloride of the formula RCl.

4. A process according to claim 1 wherein the cycloaliphatic alcohol has a six membered ring and wherein the ortho-alkyl substituent is a secondary alkyl group containing up to about 6 carbon atoms.

5. A process according to claim 4 wherein the secondary alkyl group is an isopropyl group.

6. A process according to claim 1 wherein the cycloaliphatic alcohol of B) is menthol.

7. A process according to claim 1 wherein the cycloaliphatic alcohol of B) is levo-menthol.

8. A process which comprises:
   A) mixing together:
      i) a Lucas reagent formed by a process which comprises (a) introducing gaseous anhydrous hydrogen chloride into a water solution of zinc chloride formed by dissolving at least 70 parts by weight of zinc chloride in 30 parts by weight of water to produce a solids free solution; (b) maintaining the temperature of the reaction mixture at one or more temperatures in the range of about 10° to about 60° C.; and (c) terminating the introduction of the gaseous anhydrous hydrogen chloride into the resultant reaction mixture when the molar ratio of hydrogen chloride to zinc chloride used in forming said solution is in the range of slightly above 1:1 to about 2:1; and
      ii) a cycloaliphatic alcohol of the formula ROH wherein R is a mono— or polyalkyl-substituted cycloalkyl group having from 5 to 8 carbon atoms in the ring and having a linear or branched alkyl group of up to about 12 carbon atoms substituted on one of the ortho positions of the ring relative to the ring carbon atom substituted by the hydroxyl group;
      such that a reaction mixture containing the corresponding cycloaliphatic chloride of the formula RCl is formed;
   B) resolving reaction mixture from A) into (i) an organic phase containing said cycloaliphatic chloride, and (ii) an aqueous residual catalyst phase, and separating said phases from each other;
   C) treating the aqueous residual catalyst phase with additional anhydrous hydrogen chloride to form fresh Lucas reagent; and
   D) mixing together:
      i) fresh Lucas reagent from C), and
      ii) a cycloaliphatic alcohol of the formula ROH as defined hereinabove;
      such that a reaction mixture containing the corresponding cycloaliphatic chloride of the formula RCl is formed.

9. A process according to claim 8 wherein the cycloaliphatic alcohol of A) ii) and the cycloaliphatic alcohol of D) ii) both have a six membered ring and wherein the ortho-alkyl substituent thereof is a secondary alkyl group containing up to about 6 carbon atoms.

10. A process according to claim 9 wherein the secondary alkyl group is an isopropyl group.

11. A process according to claim 9 wherein the cycloaliphatic alcohol of A) ii) and the cycloaliphatic alcohol of D) ii) are, in both cases, menthol.

12. A process according to claim 9 wherein the cycloaliphatic alcohol of A) ii) and the cycloaliphatic alcohol of D) ii) are, in both cases, levo-menthol.

* * * * *